(12) United States Patent
Smith et al.

(10) Patent No.: US 8,744,590 B2
(45) Date of Patent: Jun. 3, 2014

(54) CONFIGURING AN ELECTRICALLY STIMULATING DEVICE TO STIMULATE USING A SUBSET OF ELECTRODE CONTACTS

(75) Inventors: Zachary Smith, Englewood, CO (US); Chris van den Honert, Boulder, CO (US)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/469,912

(22) Filed: May 11, 2012

(65) Prior Publication Data
US 2013/0304157 A1 Nov. 14, 2013

(51) Int. Cl.
*A61N 1/00* (2006.01)
(52) U.S. Cl.
USPC .............................. 607/59; 607/57

(58) Field of Classification Search
USPC .................... 607/55–57, 30, 59, 62
See application file for complete search history.

(56) References Cited

U.S. PATENT DOCUMENTS

2011/0093038 A1* 4/2011 Honert ............................ 607/57
2011/0288613 A1* 11/2011 Smith et al. ...................... 607/57

* cited by examiner

*Primary Examiner* — Scott Getzow
(74) *Attorney, Agent, or Firm* — K&L Gates, LLP

(57) ABSTRACT

A method of configuring a prosthesis having two or more electrode contacts, including configuring the prosthesis to provide stimulation to a first tissue site from a subset of electrode contacts based on data based on a comparison of first data to second data, wherein the first data is based on respective estimated voltages for the first site and one or more of additional respective sites to be applied by the subset of electrode contacts, the respective estimated voltages being based on empirical stimulation data for the first and additional sites, and the second data is based on respective target voltages for the first and additional sites, respectively.

37 Claims, 12 Drawing Sheets

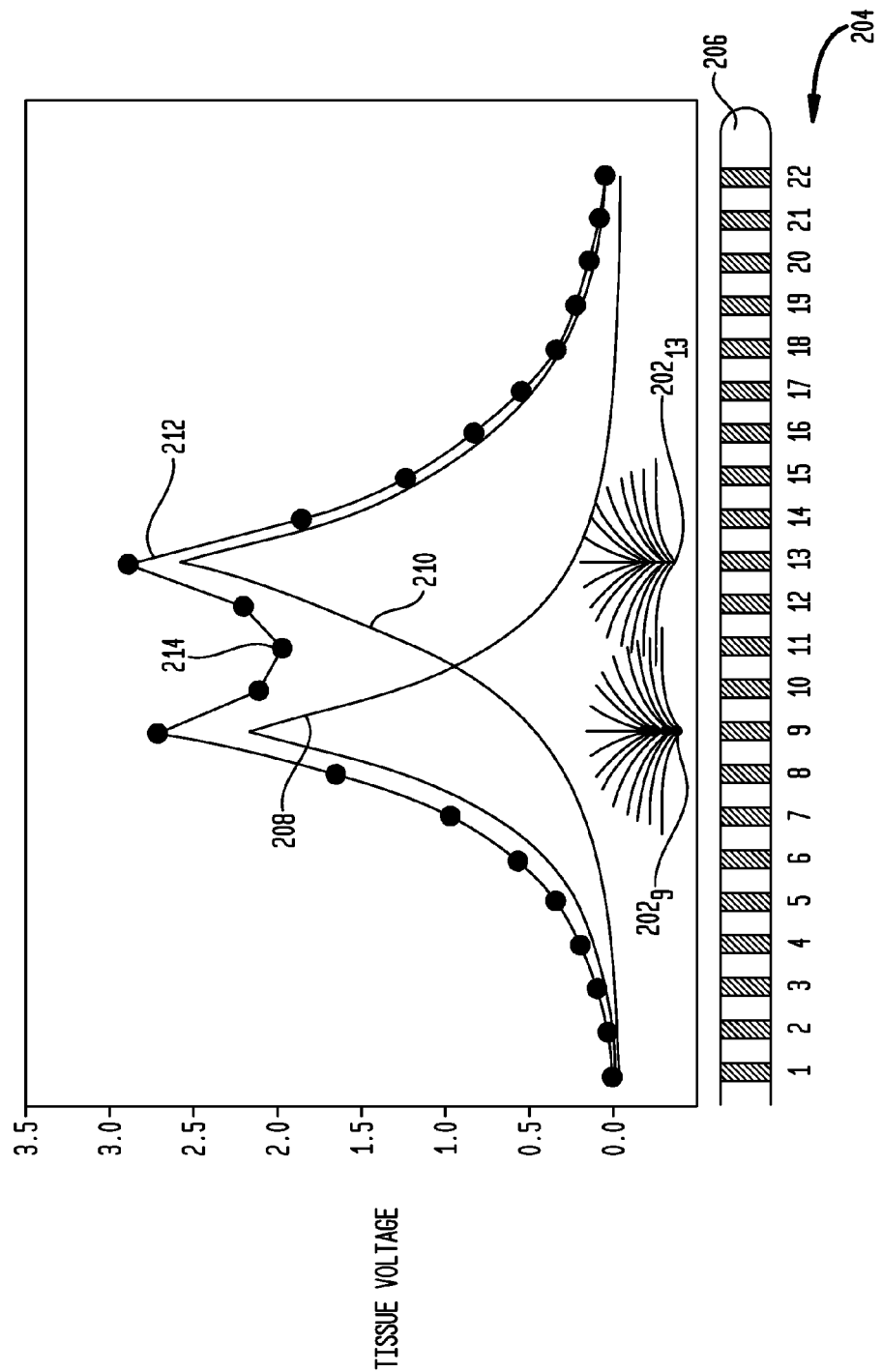

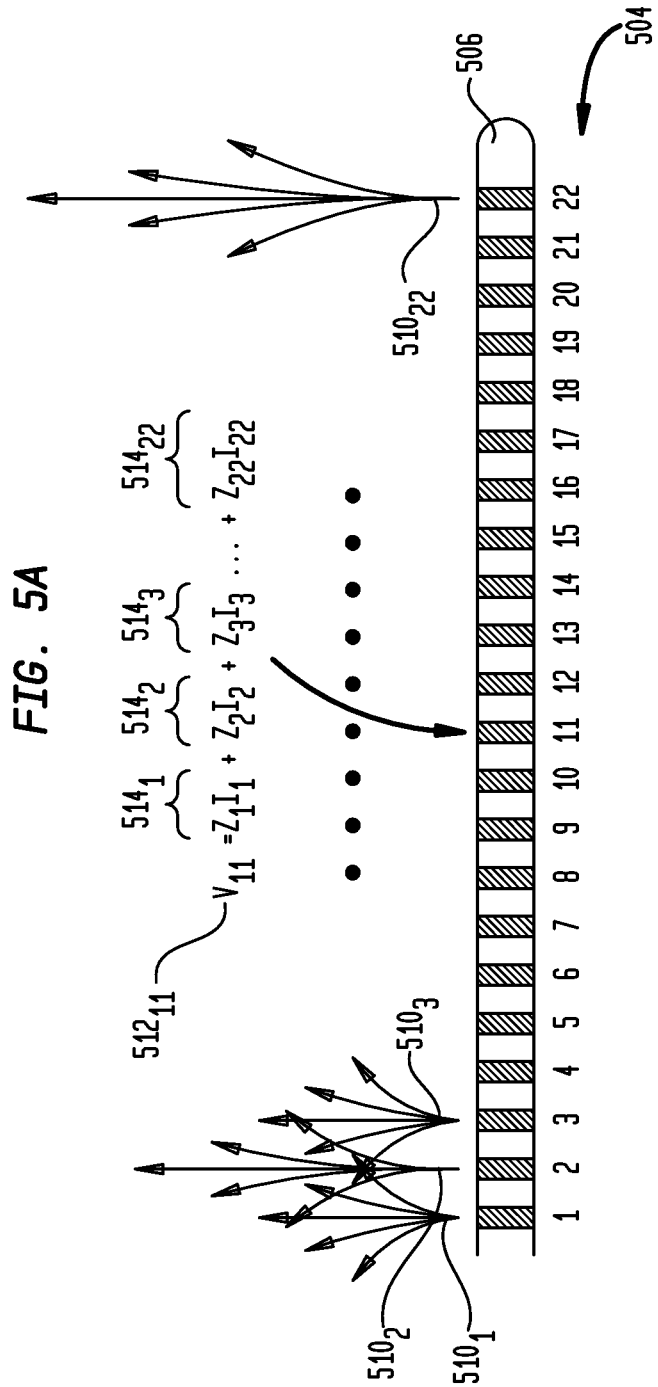

*FIG. 5B*

$$512_1 \left\{ V_1 = Z_{1,1} I_1 + Z_{2,1} I_2 + Z_{3,1} I_3 \ldots + Z_{22,1} I_{22} \right.$$

$$512_2 \left\{ V_2 = Z_{1,2} I_1 + Z_{2,2} I_2 + Z_{3,2} I_3 \ldots + Z_{22,2} I_{22} \right.$$

$$\vdots$$

$$512_3 \left\{ V_{22} = Z_{1,22} I_1 + Z_{2,22} I_2 + Z_{3,22} I_3 \ldots + Z_{22,22} I_{22} \right.$$

CONFIGURING AN ELECTRICALLY STIMULATING DEVICE TO STIMULATE USING A SUBSET OF ELECTRODE CONTACTS

BACKGROUND

There are several types of medical devices that use electrical stimulation to stimulate nerve, muscle or other tissue fibers in a recipient. Sometimes, the electrical stimulation is applied to compensate for a deficiency in the recipient. For example, electrically stimulating hearing prostheses, such as cochlear implants, have been developed to evoke a hearing percept in a recipient thereof.

In particular cochlear implants (also referred to as cochlear devices, cochlear prosthetic devices, cochlear implants, and the like; simply "cochlear implants" herein) apply one or more stimulating signals to the cochlea of a recipient to stimulate hearing.

Cochlear implants can include a sound input device that receives incoming sound, and a sound processor that converts selected portions or all of the portions of the incoming sound into corresponding stimulating signals based on an implemented sound encoding strategy. The sound processor transmits the stimulating signals along an electrode array implanted within or adjacent to the cochlea of the recipient.

Cochlear implants exploit the tonotopic organization of the cochlea by mapping audio energy in specific frequency bands to deliver stimulation at corresponding locations along the spiral array of auditory nerve fibers. To achieve this, the processing channels of the sound processor; that is, specific frequency bands with their associated signal processing paths, are mapped to a set of one or more electrode contacts of the electrode array to stimulate a desired nerve fiber or nerve region of the cochlea. Such sets of one or more electrode contacts are referred to herein as "electrode channels" or, more simply, "channels."

Another example of an electrically stimulating hearing prosthesis is an auditory brainstem implant which delivers electrical stimulation to the auditory brainstem nuclei of a recipient to evoke a hearing percept.

Some electrically stimulating prostheses deliver stimulation via a single electrode contact (mono-polar stimulation), while other electrically stimulating prostheses apply stimulation via a plurality of electrode contacts (multi-polar stimulation).

SUMMARY

An aspect of the technology detailed herein includes a method of configuring a prosthesis having two or more electrode contacts, comprising configuring the prosthesis to provide stimulation to a first tissue site from a subset of electrode contacts based on data based on a comparison of first data to second data, wherein the first data is based on respective estimated voltages for the first site and one or more of additional respective sites to be applied by the subset of electrode contacts, the respective estimated voltages being based on empirical stimulation data for the first and additional sites, and the second data is based on respective target voltages for the first and additional sites, respectively.

Another aspect of the technology detailed herein includes a method of providing configuration data for a prosthesis having a plurality of electrode contacts, comprising applying stimulation to a first stimulation site from a subset of electrode contacts of the plurality of electrode contacts, obtaining first estimated data for the stimulation applied to the first stimulation site from the subset of electrode contacts, the first estimated data based on respective transimpedance-based data for the first stimulation site and at least one additional stimulation site based on empirical results of the applied stimulation to the first stimulation site, and one or more respective target voltages for the first and additional sites, and generating configuration data for the prosthesis based on the first estimated data, wherein the prosthesis is operable to be configured by the configuration data to stimulate the first stimulation site via the subset of electrode contacts.

BRIEF DESCRIPTION OF THE DRAWINGS

Embodiments of the present technology are described herein in conjunction with the accompanying drawings, in which:

FIG. 2B is a graph illustrating a "current spread" when two electrode contacts are stimulated, along with a view of the electrode array of which the electrode contacts are apart;

FIG. 5A is a schematic of an exemplary electrode array with 22 stimulating electrode contacts according to an embodiment;

FIG. 5B depicts exemplary equations that can be used to construct stimulating and limiting signals in an exemplary embodiment;

DETAILED DESCRIPTION

Figure 1:
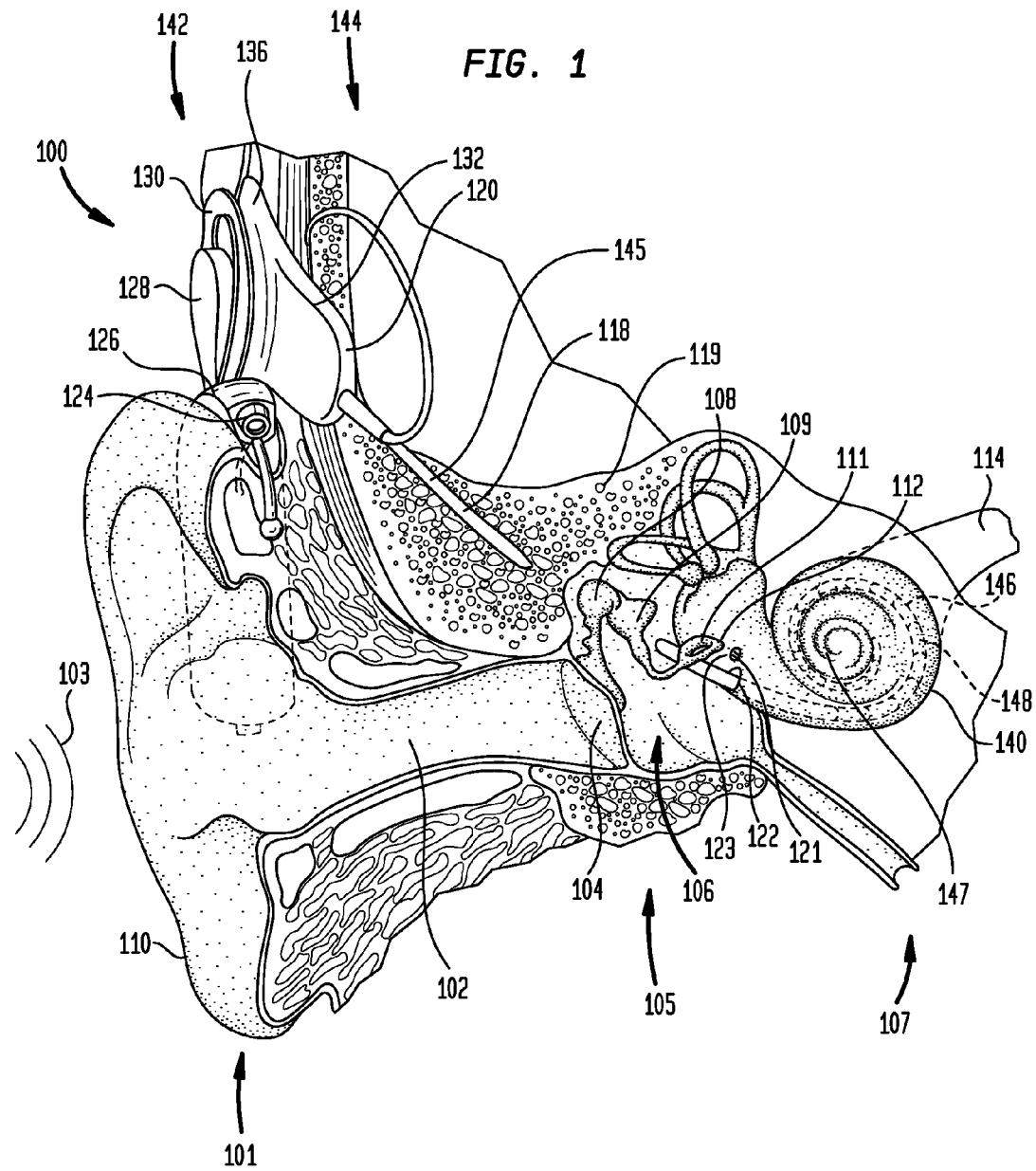
FIG. 1 is a perspective view of an exemplary stimulating medical device, a cochlear implant, in accordance with an embodiment.

FIG. 1 is a perspective view of an exemplary cochlear implant 100 implanted in a recipient having an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102 (referred to herein sometimes as the outer ear canal). An acoustic pressure or sound wave 103 is collected by auricle 110 and channeled into and through ear canal 102. Disposed across the distal end of ear cannel 102 is a tympanic membrane 104 that vibrates in response to sound wave 103. This vibration is coupled to oval window or fenestra ovalis 112 through three bones of the middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate, in response to vibration of tympanic membrane 104. This vibration sets up waves of fluid motion of the perilymph within cochlea 140. Such fluid motion, in turn, activates hair cells (not shown) inside of cochlea 140, which in turn cause appropriate nerve impulses to be generated and transferred through the spiral ganglion cells (not shown) and auditory nerve 114 to the brain (also not shown) where they are perceived as sound.

Cochlear implant 100 comprises an external component 142 that is directly or indirectly attached to the body of the recipient, and an internal or implantable component 144 that is temporarily or permanently implanted in the recipient. External component 142 typically comprises one or more sound input elements for detecting sound, such as microphone 124, a sound processing unit (not shown), a power source (not shown). Collectively, these components are part of a behind-the-ear (BTE) device 126 in the embodiment depicted in FIG. 1. External component 142 can further include a transmitter unit 128 comprising an external coil 130. Sound processing unit 126 processes the output of microphone 124 and generates encoded data signals which are provided to external transmitter unit 128.

Internal component 144 comprises an internal receiver unit 132, a stimulator unit 120, and an elongate stimulating lead assembly 118. Internal receiver unit 132 and stimulator unit 120 are hermetically sealed within a biocompatible housing commonly referred to as a stimulator/receiver unit. An internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, implanted in cochlea 140. As used herein the term "stimulating lead assembly," refers to any device capable of providing stimulation to a recipient, such as, for example, electrical or optical stimulation.

Electrode assembly 145 can be inserted into cochlea 140 via a cochleostomy 122, or through round window 121, oval window 112, and the promontory 123 or an opening in an apical turn 147 of cochlea 140. Integrated in electrode assembly 145 is an array 146 of a longitudinally aligned and distally electrode contacts 148. Stimulator unit 120 generates stimulation signals which are applied by electrode contacts 148 to cochlea 140, thereby stimulating auditory nerve 114.

Figure 2A:
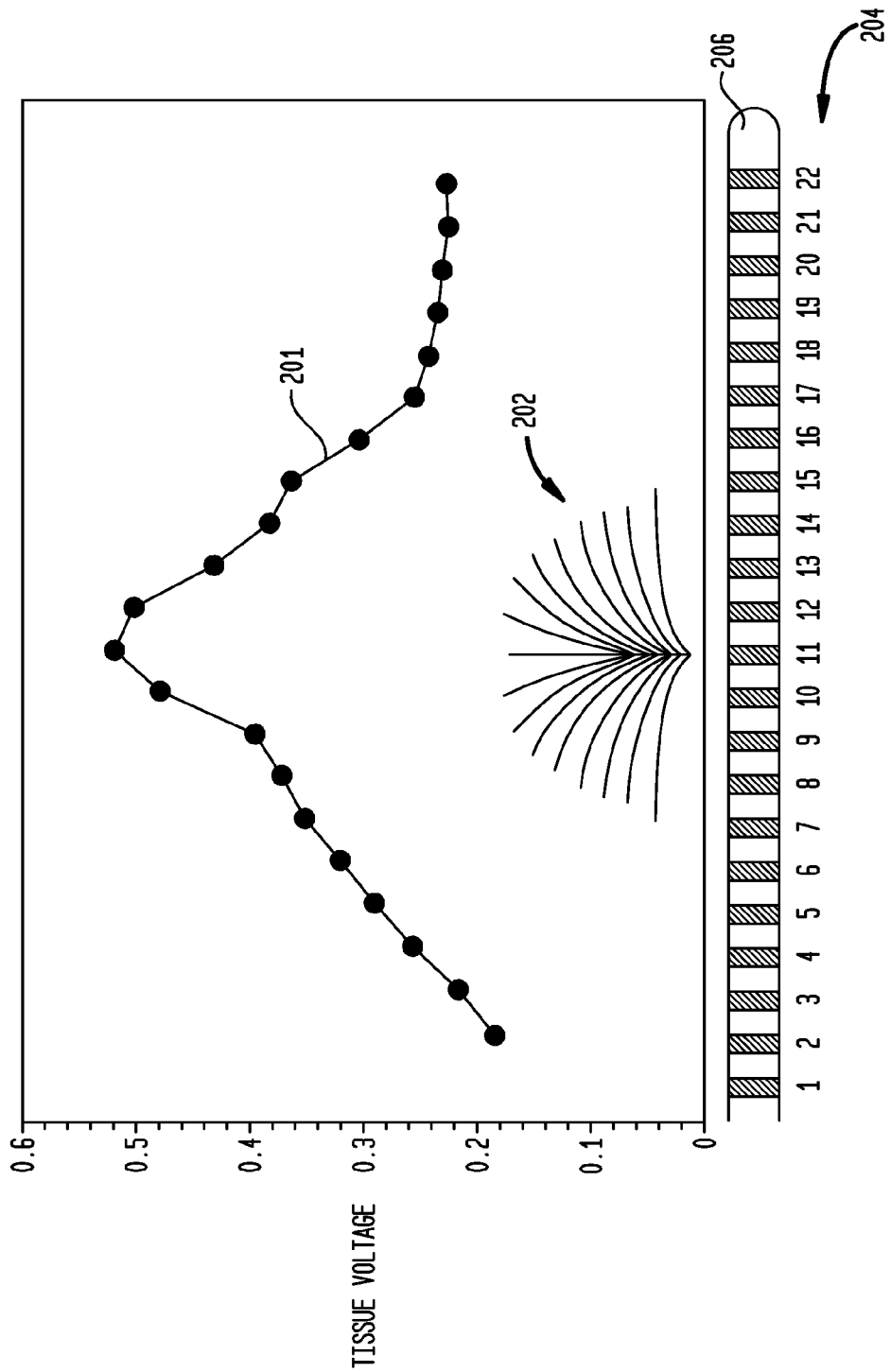
FIG. 2A is a graph illustrating the voltage generated in various regions of tissue in response to the application of current to one tissue region.

Some embodiments are directed towards cochlear implants that provide stimulation via the application of current concurrently (simultaneously or at least effectively simultaneously) to two or more electrode contacts, although embodiments can also sometimes apply current via a single electrode contact. Such embodiments can rely on the fact that some stimulation provided by cochlear implants can exhibit "current spread," which can influence the spatial resolution of multi-channel cochlear implants. In this regard, while stimulation through one channel can be intended to excite a specific nerve region, the actual locus of neural excitation can be broad and complex due the spread of current throughout the conducting fluids and tissues of the cochlea. This is illustrated by way of example in FIG. 2A, which depicts the voltage created at various electrode contacts in response to the application of current at one electrode contact. Voltage profile 201 illustrates the voltage created at different nerve regions of the cochlea ("tissue voltage") at a plurality of locations adjacent electrode contacts 204 of an electrode array 206 (correspond to array 146 of electrode assembly 145), in response to current delivered to electrode contact number 11. Superimposed on FIG. 2A is an illustration of the current spread 202 emanating from the nerve region adjacent electrode contact 11 associated with voltage profile 201.

As illustrated by voltage profile 201, current delivered by electrode contact 11 can spread over a potentially wide spatial extent of neighboring nerve regions. This current spread can extend, for example, to nerve regions adjacent to distant electrode contacts 1 and 22 of the 22 electrode contacts of electrode array 206. As a result, a stimulating voltage 201 arises not only in the nerve region adjacent electrode contact 11 but also at more distant regions in the tissue. As shown in FIG. 2A, stimulating voltage 201 is strongest or most intense near electrode contact 11, dropping off slowly and, in this example, remaining non-negligible at all regions in the cochlea nerve adjacent to electrode array 206. As a result, in addition to the nerve fibers adjacent electrode contact 11, other nerve fibers in the cochlea are stimulated by this exemplary current applied to electrode contact 11. This can produce a distributed place-pitch perception, rather than the single pitch percept.

This phenomenon can be even more pronounced when current flows concurrently from two or more electrode contacts, as can occur when representing a sound with multiple frequency components. When two or more channels are activated concurrently, the locus of excitation is not the simple union of their individual loci because of the nonlinearity of the neural excitation process. Instead, neurons that fall outside of the individual loci (i.e. those which would not respond to any one channel) can nevertheless be excited by the summed current fields.

FIG. 2B depicts an example of current spread $202_9$ and $202_{13}$ when current concurrently flows from two electrode contacts 9 and 13 of electrode array 206. Voltage profile 208 is generated in response to stimulating electrode contact 9, while voltage profile 210 is generated in response to stimulating electrode contact 13. Voltage profile 212 is the sum of voltage profiles 208 and 210; that is, voltage profile 212 is generated in response to concurrently stimulating electrode contacts 9 and 13. As shown in FIG. 2B, the combined currents produce a stimulus voltage in the nerve region adjacent to each electrode contact which is greater than intended, as well as a high voltage 214 in the nerve region between the electrode contacts 9 and 13.

This summation of stimulus voltages can have perceptual consequences, such as when many electrode contacts are activated concurrently to represent a complex sound with multiple frequency components. In some circumstances, such stimulation can result in unpredictable and/or excessive loudness and loss of spectral shape (i.e., the peaks of the frequency-place profile are distorted by the summation of fields). Some embodiments implement a cochlear implant that is configured to utilize multipolar stimulation while accounting for some and/or all of these circumstances. (In some embodiments, the cochlear implant is also configured to utilize unipolar stimulation.) That is, at least some exemplary embodiments include a cochlear implant utilizing multipolar channels to achieve focused stimulation/substantially focused stimulation that address the phenomenon associated with FIGS. 2A and 2B.

It is noted that while embodiments herein are described in terms of a cochlear implant, the teachings herein and/or variations thereof can relate to other types of tissue stimulating devices that utilize multiple electrode contacts.

More particularly, at least some of these exemplary embodiments are directed to configuring or otherwise obtaining information to configure (e.g., fit) a cochlear implant that has been configured by choosing particular subsets of electrode contacts of a set of electrode contacts that provide a desired stimulation at a desired tissue site, where various subsets of the electrode contacts with various currents applied thereto can provide different stimulations at that location. That is, by way of example, stimulation provided by a subset of electrode contacts 11 and 12 to a tissue site located in between these two electrode contacts at given currents from the electrode contacts can be different than that provided by a subset corresponding to electrode contacts 10, 11, 12 and 13 at given currents, and, depending on various factors, the former or the latter can have more desirable utility vis-à-vis evoking a hearing percept. Some embodiments are directed at determining which subset from amongst a plurality of subsets evokes a hearing percept at a given tissue location that has greater utility, as will now be described with respect to an exemplary cochlear implant. In this regard, some embodiments include technology having utility for choosing particular subsets of electrode contacts from amongst a set of electrode contacts to be used to achieve focusing at given stimulation sites. Further, some embodiments include technology having utility for choosing the respective weights for the respective currents that are to be applied to the electrode contacts of the subset of electrode contacts.

An exemplary cochlear implant applicable to some embodiments can include an electrode array having a total number of electrode contacts N (not including return or ground electrode contacts) that are variously utilized to provide controlled stimulation to a number of different sites L at which stimulation is to be controlled (which, in some embodiments, is equivalent to the number of channels to be implemented). The number of electrode contacts used to implement a channel/stimulate a given site is provided by the variable M, where M is less than the total number of electrode contacts N, and can be different for each of the L channels (i.e., the number of channels in this embodiment is equal to the number of different sites, both of which are equal to L, although in other embodiments, the number of channels may be different from the number of sites).

The term "channel" as used herein with respect to the teachings herein associated with this exemplary cochlear implant that is the subject of this discussion refers to a subset of M electrode contacts of the N electrode contacts that provide respective stimulation voltages and/or currents at M corresponding dimensionless numerical weights. Stimulation through a channel, with respect to this exemplary cochlear implant, corresponds to delivering respective electrical currents through the respective M electrode contacts of the set of electrode contacts, where the ratios of those respective currents relative to one another and/or to a unitized value can be based on the corresponding weights assigned to the respective channels.

In some embodiments, M is a constant across L channels; i.e., every channel employs the same number of electrode contacts/the subset of electrode contacts includes the same number. In other embodiments, each channel can employ a different number of electrode contacts. In that case, L values of M can be determined (one for each channel) as follows: $M_1, M_2, \ldots M_L$.

Figure 3:
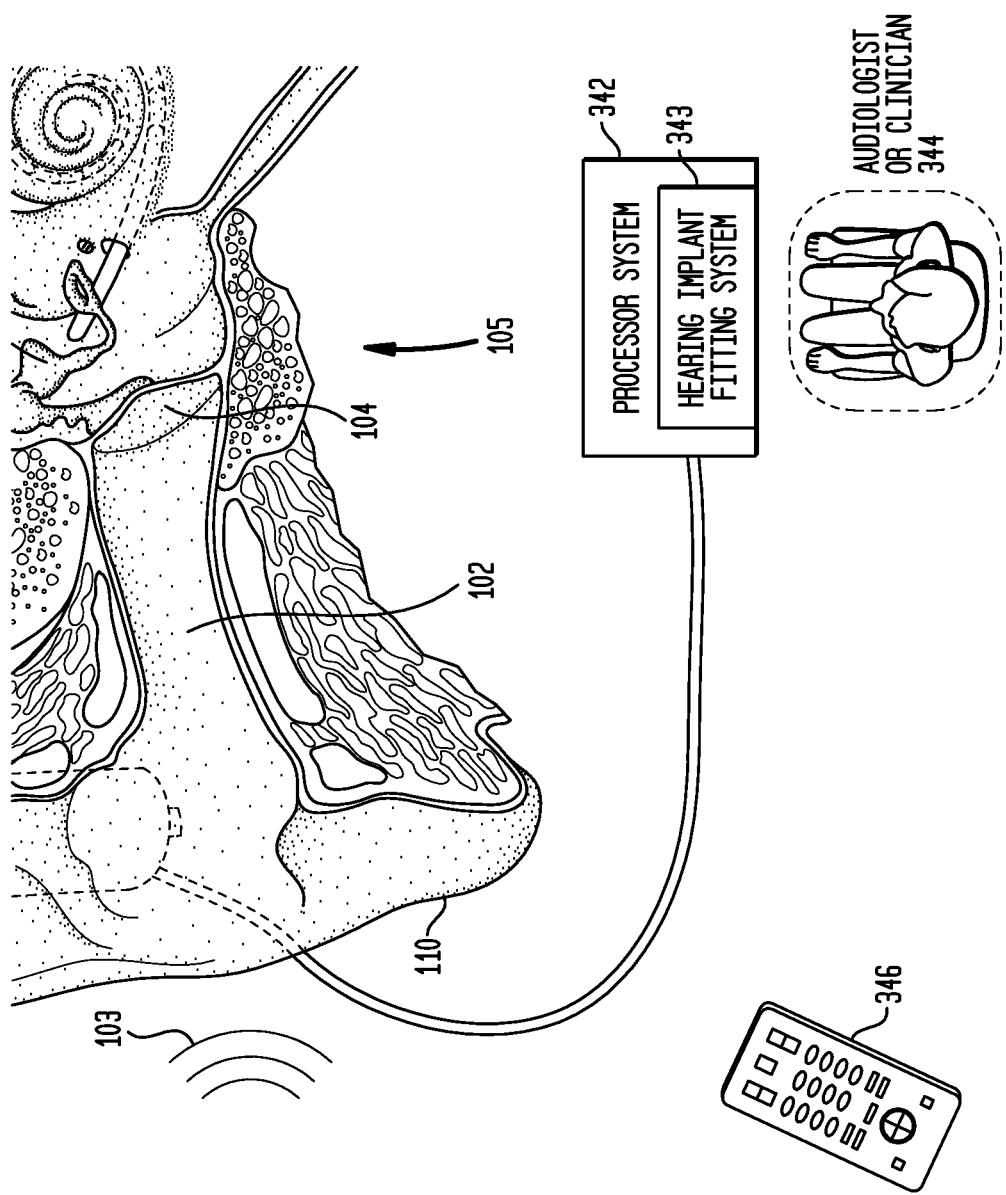
FIG. 3 is a schematic of an exemplary fitting system according to an exemplary embodiment.

To obtain configuration data for the exemplary cochlear implant, empirical data is obtained from the cochlear implant after implantation into a recipient. In this regard, FIG. 3 depicts a fitting system 343 of a processor system 342, operated by an audiologist 344, in communication with the cochlear implant 100 described above with respect to FIG. 1. Accordingly, some embodiments of cochlear implant 100 are configured to interoperate with a wireless user interface 346 to facilitate implant configuration and control by the recipient and/or other personnel, and an external processor 342 such as a personal computer, workstation or the like, implementing the hearing implant fitting system 343. The external processor 342 can be used to obtain the configuration data, as will now be described by way of example.

Figure 4:
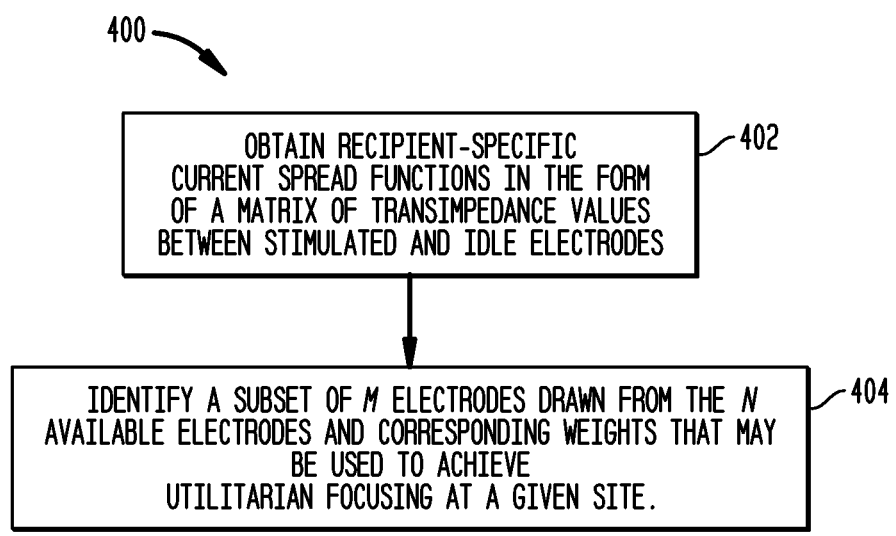
FIG. 4 is a flowchart illustrating an exemplary method.

FIG. 4 is a high-level flow chart of operations performed in accordance with an exemplary embodiment of a method 400 for obtaining the configuration data. The operations will now be described with additional reference to FIGS. 5A and 5B.

At step 402 of method 400, recipient-specific current spread functions in the form of a matrix of transimpedance values between stimulated and idle electrode contacts is obtained. These values can be obtained during the method, or previously obtained, utilizing processor 342, where an audiologist or other personnel measures recipient-specific current spread functions in the form of a matrix of transimpedance values between stimulated and idle electrode contacts. Specifically, for each intracochlear electrode contact, a monopolar biphasic pulse is delivered via the cochlear implant 100 controlled by or otherwise prompted by processor 342. When a mono-polar current is passed through an intracochlear electrode contact 504 (FIG. 5A) a corresponding voltage can be measured at any other intracochlear electrode contact 504, this measurement being obtained via processor 342. The transimpedance between the two electrode contacts, defined herein as the ratio of the measured voltage to the delivered current, can be identified. For frequencies of interest in cochlear applications, the cochlear fluids and tissue are essentially resistive such that the voltage is approximately instantaneously proportional to the current to a close approximation. Thus the reactive component of the transimpedance can be ignored. It is noted that the analysis presented herein can be carried out with complex arithmetic in those applications in which reactive components are nonnegligible.

For each intracochlear electrode contact 504, a monopolar biphasic pulse is delivered at the maximum comfortable current level. Return current is measured, for example, at one or more extra-cochlear electrode contacts. The voltage pulse at each of the remaining electrode contacts 504 is measured. In an exemplary embodiment, the phase width is selected to be long enough for the voltage pulse waveform to plateau, but short enough to permit relatively high currents while remaining comfortable, thus maximizing the signal-to-noise ratio of the voltage measurement. Based on the applied current and measured voltage, the transimpedance of each combination of electrode contacts is determined as described below.

Referring to FIG. 5A, each current $I_1$ through $I_{22}$ flowing concurrently through the 22 different electrode contacts 504 results in a current spread $510_1$ through $510_{22}$, respectively. The instantaneous voltage 512 ($V_1 \ldots V_{22}$) adjacent to each electrode contact 504 is the sum of 22 separate components $514_1$ through $514_{22}$. Each component 514 is proportional in magnitude and sign to the current from one of the electrode contacts 504 $I_1 \ldots I_{22}$ (in units of mA), represented by the corresponding measured transimpedance value, $Z_1$ $Z_{22}$ (in units of V/mA (kΩ.)). Thus the stimulating voltage $512_{11}$ at the site of electrode contact 11 can be expressed as a weighted sum of the weighted currents through all stimulating electrode contacts, as shown in FIG. 5A and Equation (1) below:

$$V_{11} = Z_1 I_1 + Z_2 I_2 + \ldots Z_{22} I_{22} \qquad (1)$$

A similar equation for the voltage adjacent to each of the other electrode contacts 504 is shown in FIG. 5B. Thus, in a 22 electrode contact system, 22 simultaneous equations can be written which describe the voltage applied to the nerve region adjacent to each electrode contact as a weighted sum of the same set of 22 currents $I_1 \ldots I_{22}$. The set of 22 simultaneous equations in FIG. 5B, where each weight and transimpedance Z has two subscripts, one indicating the associated current, and one indicating the electrode contact site whose voltage is being summed. The set of simultaneous equations in FIG. 5B, can be represented in vector/matrix notation as shown in Equation (2):

$$V = ZI_e \qquad (2)$$

where $I_e$ represents the column vector of 22 currents $I_1 \ldots I_{22}$ flowing through the electrode contact, Z represents the square matrix of weights $z_{1,1} \ldots z_{22,22}$, and V represents the column vector of 22 stimulating voltages $V_1 \ldots V_{22}$ at the discrete stimulation regions adjacent the corresponding electrode contacts $I_1 \ldots I_{22}$.

As noted, both the currents and voltages are represented as functions of time, indicating that the matrix equation represents an instantaneous calculation. It should be appreciated, however, that as noted above, an embodiment can utilize simple scalar values. This reflects the assumption that voltages are instantaneously proportional to currents (equivalent to assuming that the tissue impedances is purely resistive with no reactive component). If a current changes, all resulting voltages change instantaneously and proportionally. While this is a relatively accurate approximation, it is not exactly correct. At the expense of greatly increased computational burden, embodiments of the invention can be practiced using complex values in the matrices, recognizing the reactive (non-resistive) part of the relationship between currents and voltages. Instead of being functions of time, the variables in equations 1 and 2 would be functions of the Laplace transform variables.

For a stimulating electrode contact j and measuring electrode contact i, transimpedance $z_{ij}$ has units of V/mA (kΩ) and is given by Equation (3):

$$z_{ij} = v_i / i_j \qquad (3)$$

where, $v_i$ is the measured peak voltage at measuring electrode contact i, and $i_j$ is the amplitude of the current pulse applied to electrode contact j. In this way a 22×22 matrix $Z_m$ of transimpedance values can be determined for each recipient, as shown in Equation (4):

$$Z_m = \begin{bmatrix} z_{1,1} & z_{1,2} & \cdots & z_{1,22} \\ z_{2,1} & z_{2,2} & \cdots & z_{2,22} \\ \vdots & \vdots & \ddots & \vdots \\ z_{22,1} & z_{22,2} & \cdots & z_{22,22} \end{bmatrix} \qquad (4)$$

Each column p of equation 4 (each column of the matrix) represents the spread function for stimulation through electrode contact p, with a peak at a given diagonal value of $Z_m$. The values on the diagonal of $Z_m$ typically can not be measured explicitly due to polarization effects. A current-carrying electrode contact is polarized by electrochemical gradients that arise across the metal/electrolyte boundary. This precludes using the same electrode contact both to deliver current and to measure potential in the cochlear fluid. Instead, values on the diagonal can be extrapolated, preferably using the highest slope among adjacent pairs in the same row and column to avoid underestimating the sharpness of the spread function, as this would result in unnecessarily high peak currents in the focused stimuli. The effect of errors among the extrapolated values is considered below.

The matrix $Z_m$ is very nearly diagonally symmetric. For example, for a three-port network where a single node serves as both the return current path and the voltage measurement reference, the reciprocity theorem holds that diagonal symmetry obtains, (i.e. $z_{ij} = z_{ji}$ for all i and j).

Due to the noted polarization phenomenon, the extracochlear electrode contact contacts can not be able to serve as both return current path and voltage reference. Instead, a surface electrode contact on the recipient can serve as the reference. However the observed deviations from diagonal symmetry were small and comparable to the noise in the measurements. This implies that the tissue adjacent the return electrode contact is essentially neutral, or equipotential with the external electrode contact, and that the voltage gradients of consequence occur within and about the cochlea. Therefore it can be assumed that deviations from diagonal symmetry are dominated by noise in the measurement. In order to reduce this noise the diagonally opposite elements can be averaged to compute a new transimpedance matrix, as shown in Equation (5):

$$Z = \frac{1}{2}(Z_m + Z_m^T) \qquad (5)$$

where $Z_m^T$ denotes the transpose of $Z_m$ (matrix Z is diagonally symmetric by definition).

Certain embodiments can rely on the utility of Reciprocity Theorem to avoid measuring the entire forward matrix [z], omitting measurement of cells above the main diagonal of matrix [z]. The unmeasured values are then filled in by transposing values from below the main diagonal. Alternatively, embodiments can omit the measurement of cells below the main diagonal, and fill these measurements by transposing values from above. In either case such embodiments can reduce the number of measurements needed to determine matrix [z] by half.

As seen above, the matrix Z is a square matrix (i.e., it has the same number of rows and columns). In this regard, the Z matrix detailed above corresponds to a cochlear implant with N stimulating electrode contacts and N corresponding stimulation sites (channels), where a set of N weight vectors is determined, which vectors achieve focusing at each of the N sites. However, in some embodiments, the cochlear implant focuses stimulation at L sites, where L>N.

Thus, in some embodiments, the matrix Z can be an N×N transimpedance matrix or can be a L×N transimpedance matrix, where the transimpedance for each site other than electrode contacts sites can be determined through interpolation or extrapolation (or any other manner that will permit embodiments detailed herein and/or variations thereof to be practiced) from those at nearby electrode contact sites.

In some embodiments, the transimpedance matrix can be a modified transimpedance matrix as can be modified to permit embodiments detailed herein and/or variations thereof to be practiced. It can be a matrix relating radial current density at L sites in Rosenthall's canal to N stimulating currents. Accordingly, in some embodiments, the matrix Z can represent an output parameter of interest at each of L sites as a linear combination of N currents through the electrode contacts.

The use of a matrix can be a matter of convenience, and in some embodiments, the transimpedance data can not be in the form of a matrix, but instead can be in the form of arrays or tables or the like. Any form in which transimpedance data can be presented that permits embodiments detailed herein and/or variations thereof to be practiced can be used in some embodiments. It is further noted that step 402 can be accomplished in any manner that provides transimpedance data, such as, for example, retrieving the data from a memory or the like, where the data was previously obtained by an audiologist using the processor system 342. Any device, system and/or method to obtain the transimpedance data can be used in some embodiments providing that the teachings detailed herein and/or variations thereof can be implemented.

By way of example, below is an exemplary transimpedance matrix for an exemplary implanted cochlear implant, such as the cochlear implant that is the topic of the present example, having five (5) electrode contacts (N=5), where it is desired to configure the implanted cochlear implant to implement nine channels (L=9) (delivering stimulation to nine sites (the five electrode contact sites and four intermediate sites between the electrode contacts)).

$$Z = \begin{bmatrix} z_{1,1} & z_{1,2} & \cdots & z_{1,5} \\ z_{2,1} & z_{2,2} & \cdots & z_{2,5} \\ \vdots & \vdots & \ddots & \vdots \\ z_{9,1} & z_{9,2} & \cdots & z_{9,5} \end{bmatrix} = \begin{bmatrix} 5.0 & 3.0 & 1.0 & 1.5 & 0.5 \\ 3.5 & 4.0 & 1.5 & 1.6 & 0.6 \\ 2.6 & 6.0 & 2.1 & 1.7 & 0.7 \\ 2.3 & 3.8 & 2.9 & 2.0 & 0.9 \\ 2.2 & 2.8 & 4.1 & 2.5 & 1.1 \\ 2.1 & 2.3 & 3.0 & 3.0 & 1.5 \\ 2.0 & 2.1 & 2.4 & 4.5 & 2.0 \\ 1.9 & 2.0 & 2.0 & 2.7 & 3.0 \\ 1.9 & 1.9 & 1.8 & 2.0 & 5.0 \end{bmatrix}$$

Figure 6:
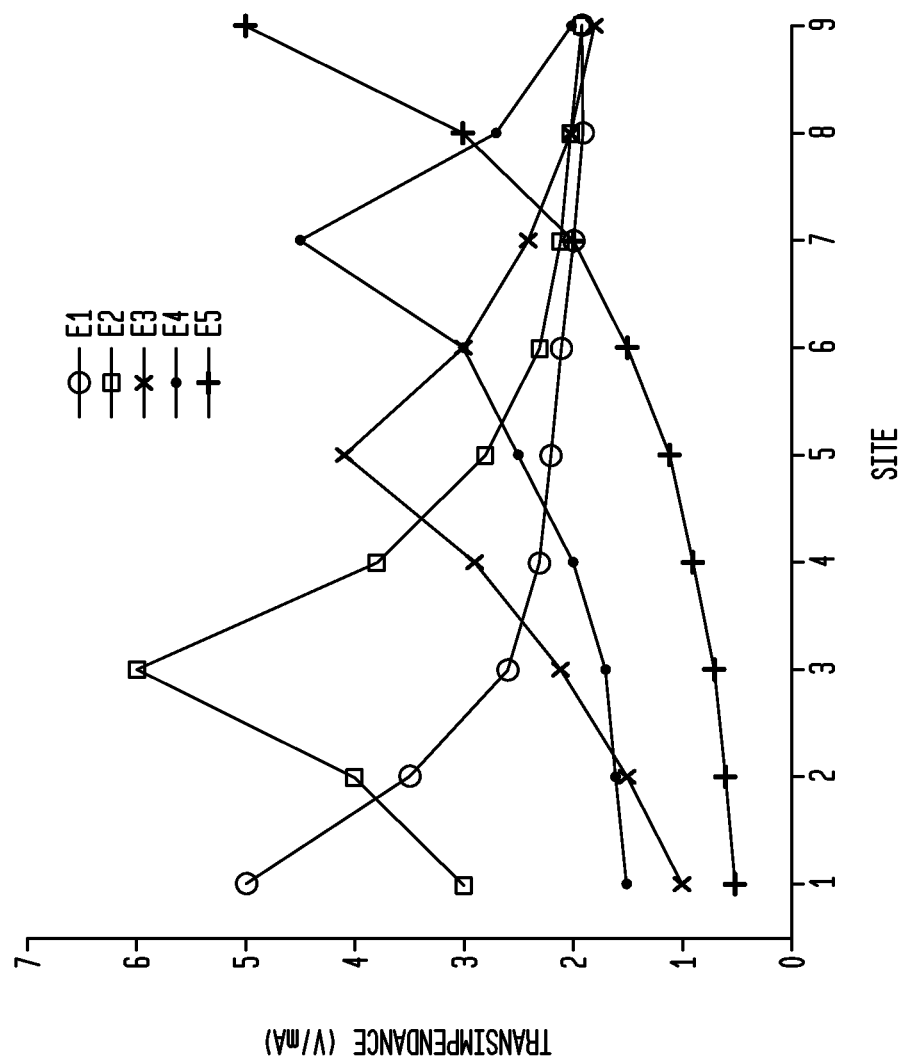
FIG. 6 a graph illustrating a current spread function for five electrode contacts (N=5) across nine stimulation sites (L=9)

In an exemplary embodiment, the above 9×5 transimpedance matrix Z can be determined from direct voltage measurements at electrode contacts 1 through 5 (rows 1, 3, 5, 7, and 9) and by curve fitting/interpolation for rows 2, 4, 6 and 8. If it were desired to implement five channels (L=5), the matrix would be a 5×5 matrix corresponding to rows 1, 3, 5, 7 and 9 of the above matrix. Column 1 of Z represents the spread function of electrode contact 1, column 2 represents the spread function of electrode contact 2, etc. Those spread functions are plotted in FIG. 6.

Values $z_{1,1}, z_{3,2}, z_{5,3}, z_{7,4}, z_{9,5}$ can be extrapolated or otherwise estimated. Any device, system and/or method that will permit values for values $z_{1,1}, z_{3,2}, z_{5,3}, z_{7,4}$, and/or $z_{9,5}$ to be obtained can be used in some embodiments providing that the teachings herein and/or variations thereof can be implemented.

Having established or otherwise obtained the transimpedance matrix Z in particular, or transimpedance data in general, method 400 proceeds to step 404, which entails identifying a subset of M electrode contacts of the N available electrode contacts that can be used to achieve a utilitarian level of focusing at a given site, where M<N, to achieve utilitarian focusing at each of the N sites. Particularly, a subset of M electrode contacts drawn from the N available electrode contacts can be used to achieve a utilitarian level of focusing at a given site. Use of fewer than all electrode contacts for at least one channel can reduce the number of calculations required to determine each stimulus. Such can also or alternatively reduce circuit complexity by, inter alia, reducing the number of current sources, switches, data paths, registers etc. Such can further or alternatively reduce the amount of memory required to store weights and associated data for each channel. Such can further or alternatively reduce the amount of data that is to be transmitted from an external sound processor/encoder in a cochlear implant implementation.

More particularly, for one or more or all of the L channels to be implemented, a subset of M electrode contacts can be chosen where M<N≤L. Below is presented a method for choosing a subset of M electrode contacts for various channels according to an exemplary embodiment, where, to determine a full set of channels, the procedure can be repeated L times, once for each channel. In this regard, FIG. 7 details an expanded method 700 that is related to method 400, where step 710 corresponds to step 402 of method 400, steps 720, 730, 740, 750, 760, 770 and 780 correspond to step 420 of method 400, and the remaining steps are directed towards execution of method step 404 for each channel.

Briefly, it is noted that method 400 and method 700 can be implemented by the exemplary cochlear implant. This can be the case where the transimpedance data has already been developed by an audiologist and the data is retrieved from a memory of the cochlear implant. It is further noted that the methods detailed herein can be streamlined or truncated, at least with regard to the individual steps. While describing method 700, some variations to the method 700 will also be described. However, these variations are not exhaustive. Any method that achieves the information or variations thereof that results from the method 700 that permits the teachings herein and/or variations thereof to be practiced can be used.

Referring back to method 700, step 720 entails picking a channel, such as one that has not yet been evaluated. Step 730 entails determining all possible subsets K of N electrode contacts for a subset having a selected number of electrode contacts M (where M can be any number including 1 to N−1). In an exemplary embodiment, step 730 starts at M=1 and increases by 1 every time step 730 is executed (owing to the loop of which step 730 is apart, as detailed below), until M=N−1.

For a given value of M, there are K possible subsets of M electrode contacts out of the total N available, where K can be given by:

$$K = \binom{N}{M} = \frac{N!}{(N-M)!M!} \tag{1}$$

In some embodiments, some such subsets are selected for analysis, while in other embodiments, all such subsets are selected for analysis. For computational efficiency, the analysis can exclude some subsets. For example, a priori knowledge can indicate that a particular subset is a poor candidate, such as a subset of electrode contacts all of which are spatially distant from the center site of the channel. Such a subset can have been previously determined to be unlikely to provide utilitarian focusing at that site, and thus can be discounted. Of course, in other embodiments, such as those where processor time is not a controlling factor, all such subsets can be evaluated. Accordingly, a variation of step 730 can include determination of less than all K possible subsets of N for a given number M of electrode contacts. Thus, step 730 can instead or in addition to this include a determination of subsets that are not to be considered and/or a determination subsets that are only to be considered (at least for the individual occurrence of this step within the broader method 700, which can include repeating step 730 more than once in the case of an electrode array having more than two electrode contacts).

With respect to the exemplary transimpedance matrix presented above, if M=3 (where, in some embodiments, method 700 only evaluates subsets having three or more electrode contacts, where in some embodiments, method 700 only evaluates subsets having an odd number of electrode contacts, etc.) to determine the three-electrode contact channel (M=3) that produces focusing at the site of electrode contact 3 deemed to have the most utilitarian value, this site corresponding to row 5 of Z, there are ten possible subsets of 3 electrode contacts:

$$K = \binom{5}{3} = \frac{5!}{(5-3)!3!} = \frac{120}{12} = 10 \quad (3)$$

Those ten subsets are tabulated below in TABLE 1 below.

TABLE 1

| Subset # (k) | E1 | E2 | E3 | E4 | E5 |
|---|---|---|---|---|---|
| 1  | X | X | X |   |   |
| 2  | X | X |   | X |   |
| 3  | X | X |   |   | X |
| 4  | X |   | X | X |   |
| 5  | X |   | X |   | X |
| 6  | X |   |   | X | X |
| 7  |   | X | X | X |   |
| 8  |   | X | X |   | X |
| 9  |   | X |   | X | X |
| 10 |   |   | X | X | X |

In some embodiments, some subsets can be discounted or otherwise disregarded without further analysis thereof. In this regard, referring to the present example, because it is unlikely that subsets not including electrode contact 3 (i.e. #2, #3, #6, and #9), which is the closest electrode contact to site 5, will produce focusing at the site of electrode contact 3 having utility as desirable as the utility afforded by subsets including electrode contact 3, in some embodiments, these subsets can be dismissed or otherwise not included as a possible subset of the number of subsets k (thus, subsets of electrode contacts $e_k$). In a similar vein, because it is unlikely that subsets not including electrode contacts 4 or 5 will produce focusing at the site of electrode contact 3 having utility as desirable as the utility afforded by subsets including such electrode contacts, in some embodiments, these subsets can also be dismissed or otherwise not included as a possible subset of the number of subsets k. However, in other embodiments, such as where processing time and/or power is not a controlling factor, all ten subsets can be selected for analysis. In an exemplary embodiment, a figure-of-merit is to be determined for each, as will be explained further below. However, it is noted that in some embodiments, figures-of-merit need not be determined if there are other ways to evaluate which subset affords a desired utility.

After step 730 is executed, step 740 is executed, which entails picking and analyzing a subset k from amongst the possible subsets K. With respect to the above table, the following concentrates on determining a figure-of-merit for subset k=4 (the highlighted subset), as the first three subsets have been discounted for the just detailed reasons. That is, the first subset picked and analyzed in step 740 is subset #4, as subset #1, #2 and #3 have been disregarded without analysis. Analysis of the picked subset can entail determining input currents for the given subset for target voltage(s) to be applied at respective sites, determining actual voltages that will be applied at the respective sites using the given subset, and comparing the actual voltages to the target voltages to identify a figure of merit for the subset, as will now be detailed.

For the selected subset k, a reduced L×M matrix $Z_k$ can be created by deleting from the original matrix Z the columns associated with electrode contacts not included in the subset. In other embodiments, the full matrix can be utilized, where the electrode contacts not used have columns with zero values. Continuing with the present example, because electrode contacts 2 and 5 are not included in subset #4, columns 2 and 5 can be deleted from the original matrix Z to produce $Z_4$ shown in Equation (6), which is applicable to subsets #1 to #10.

$$Z_4 = \begin{bmatrix} z_{1,1} & z_{1,3} & z_{1,4} \\ z_{2,1} & z_{2,3} & z_{2,4} \\ \vdots & \vdots & \vdots \\ z_{9,1} & z_{9,3} & z_{9,4} \end{bmatrix} = \begin{bmatrix} 5.0 & 1.0 & 1.5 \\ 3.5 & 1.5 & 1.6 \\ 2.6 & 2.1 & 1.7 \\ 2.3 & 2.9 & 2.0 \\ 2.2 & 4.1 & 2.5 \\ 2.1 & 3.0 & 3.0 \\ 2.0 & 2.4 & 4.5 \\ 1.9 & 2.0 & 2.7 \\ 1.9 & 1.8 & 2.0 \end{bmatrix} \quad (6)$$

An M×L pseudo-inverse matrix $Y_k$ (or true inverse matrix for a square matrix) of matrix $Z_k$ is determined using, for example, a Moore-Penrose transformation other suitable algorithm. This matrix $Y_k$ represents a vector of input currents at each of M electrode contacts as a linear combination of L desired output values, and represents transadmittance data (as opposed to transimpedance data). With regard to the matrix $Z_4$, the Moore-Penrose pseudo-inverse $Y_4$ of matrix $Z_4$ is determined to be as shown in Equation (7).

$$Y_4 = z_4^- = \begin{bmatrix} y_{1,1} & y_{1,2} & \cdots & y_{1,9} \\ y_{2,1} & y_{2,2} & \cdots & y_{2,9} \\ y_{3,1} & y_{3,2} & \cdots & y_{3,9} \end{bmatrix} = \begin{bmatrix} .170 & .092 & .038 & .003 & -.035 & .031 & -.059 & -.014 & .006 \\ -.113 & -.029 & .056 & .136 & .245 & .052 & -.177 & -.046 & -.001 \\ -.024 & -.028 & -.055 & -.090 & -.146 & .032 & .287 & .100 & .030 \end{bmatrix} \quad (7)$$

Therefore, given an L-length vector of target outputs $V_t$, an M-length vector of input currents I can be determined from $I = Y_k V_t$. With regard to the present example, target outputs $V_t = [v_{t1} \ldots v_{tL}]$ is defined as 1 at channel center (site l=5 for electrode contact 3) with 0 elsewhere, and is shown in Equation (8) below.

$$V_t = \begin{bmatrix} v_{t1} \\ v_{t2} \\ v_{t3} \\ v_{t4} \\ v_{t5} \\ v_{t6} \\ v_{t7} \\ v_{t7} \\ v_{t9} \end{bmatrix} = \begin{bmatrix} 0 \\ 0 \\ 0 \\ 0 \\ 1 \\ 0 \\ 0 \\ 0 \\ 0 \end{bmatrix} \quad (8)$$

The vector of currents I is computed as shown in Equation (9).

$$I = Y_4 V_t = \begin{bmatrix} -.035 \\ .245 \\ -.146 \end{bmatrix} \quad (9)$$

The variable $I_{tk}$ is used herein to represent current profiles based on the target profiles for a given subset.

When these M currents are applied to the electrode contacts of the subset, the vector of L actual outputs $V_a$ can be computed from $V_a = Z_k I$. With regard to the present example, the resulting vector of actual outputs $V_a$ generated with those currents I is computed as shown in Equation (10).

$$V_a = Z_4 I = \begin{bmatrix} v_{a1} \\ v_{a2} \\ v_{a3} \\ v_{a4} \\ v_{a5} \\ v_{a6} \\ v_{a7} \\ v_{a8} \\ v_{a9} \end{bmatrix} = \begin{bmatrix} -.148 \\ .012 \\ .176 \\ .339 \\ .564 \\ .225 \\ -.136 \\ .031 \\ .084 \end{bmatrix} \quad (10)$$

Thus, the estimated voltages are based on data based on a manipulated transimpedance data matrix manipulated into a format for a solution of current vectors according to Ohm's Law (i.e., $Y_k$) multiplied by the transimpedance data matrix $Z_k$.

It is noted that the variable $V_{elk}$ as used herein refers to respective estimated stimulation profiles for sites l for a given subset k. In this regard, $V_e$ can be considered as the same as $V_a$. In view of the above, it can be seen that the process for selecting the subset of electrode contacts from which stimulation is to be provided to a given site is based on data based on a comparison of (i) data based on respective estimated voltages (i.e., actual voltages $V_a$, which, because they are calculated, are estimated voltages) for the first site and one or more of additional respective sites to be applied by the subset of electrode contacts, the respective estimated voltages being based on empirical stimulation data (e.g., the transimpedance matrix, the inverse and/or pseudo-inverse thereof, etc.) for the first and additional site, and (ii) data based on respective target voltages for the first and additional sites (i.e., $V_{tl}$). It is noted that as used herein, the phrase transimpedance-based data includes the data forming all or part of the transimpedance matrix, the inverse and/or pseudo-inverse of the transimpedance matrix, and/or the data resulting from the multiplication of these matricies together (e.g., $Z_k Y_k$). This as contrasted to the phrase transimpedance data as used herein, which only includes the data forming all or part of the transimpedance matrix. With respect to $Z_k Y_k$, in an exemplary embodiment, $V_a = Z_k Y_k V_l$, and, accordingly, the data on which the respective estimated voltages are based on is based on the multiplication of the multiplied transimpedance data and transadmittance data by the respective target voltages for the first and additional respective sites.

For each selected subset k, a figure-of-merit $\epsilon_k$ can be determined. The figure-of-merit can be related to a desired utility of the subset (e.g., how closely a set of actual output values correspond to a set of target output values). One possible figure-of-merit is the root-mean-square difference between the L target outputs and the L actual outputs. In such an scenario, the smaller the figure of merit, the closer the match between target and actual outputs, and thus the closer the match between the actual utility and the desired utility of that subset. It is noted that this is but one example of a measure of utility. Other embodiments can utilize other measures of utility. Any device, system or method that will enable an evaluation of the utility of a given subset as compared to that of another given subset can be utilized in some embodiments provided that such use permits the teachings detailed herein and/or variations thereof to be implemented.

Figure 8:
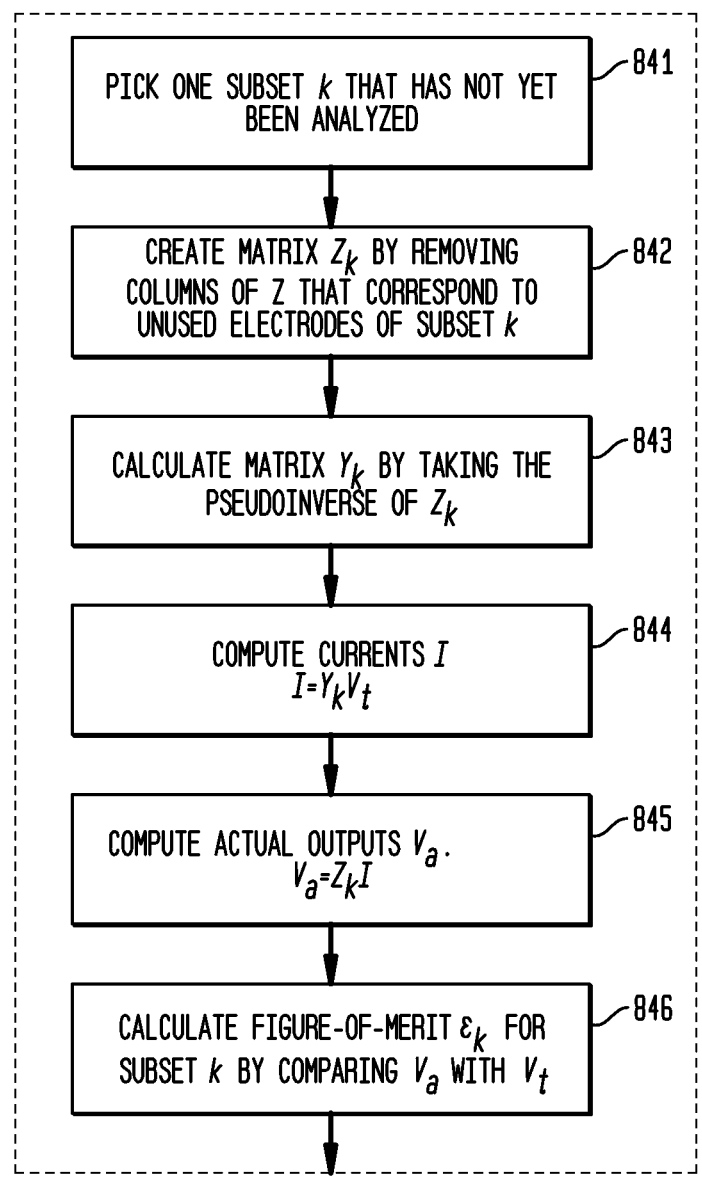
FIG. 8 is a flowchart illustrating methods for selecting and analyzing a subset k according to an exemplary embodiment.

FIG. 8 presents a flow chart 800 representing method steps for step 740. At step 841, a subset k that has not yet been analyzed is picked. At step 842, a matrix $Z_k$ is created, which can be done by removing columns of Z that correspond to the unused electrode contacts of subset k. At step 843, the pseudo-inverse of matrix $Z_k$ is determined as matrix $Y_k$. At step 844, a current matrix I is computed as the product of $Y_k$, and target response voltage vector $V_t$. In step 845, the matrix Va of voltages that would result at the various sites L is computed as a product of $Z_k$ and I. In step 846, a figure-of-merit is determined as a function of $V_a$ and $V_t$, for example, by calculating $\epsilon_k$.

Proceeding to step 750, if all K subsets of interest have not been analyzed (e.g., in some embodiments, this excludes subsets that are perceived to have utility that is not as desirable as the estimated utility of other subsets, while in other embodiments, this includes all subsets), the method returns back to step 440. If all K subsets of interest have been analyzed, the method proceeds to step 760, which entails choosing the subset for a channel having a figure-of-merit that is indicative of the desired utility (e.g., how closely the actual output values correspond to a set of target output values). In this regard, because a figure-of-merit can be computed for each selected subset k, the subset with the figure-of-merit having utility that corresponds to the desired utility can be selected for the channel. Some subsets can be excluded from consideration for practical reasons or for computational efficiency. For example if one electrode contact has a high impedance, or is to be reserved for evoked potential measurements, subsets that include that electrode contact can be excluded. Or some subsets can have weights in $Y_k$ that imply high power consumption, such as large weights that alternate in sign across sites.

With regard to the present example, a figure-of-merit $\epsilon_4$ for subset 4 is computed as the across-site root mean square (RMS) difference between target and actual outputs as shown in Equation (11).

$$\varepsilon_4 = \sqrt{\frac{1}{L}\left(\sum_{s=1}^{L}(v_{ts} - v_{as})^2\right)} = 0.220 \quad (11)$$

While the present example has disregarded evaluation of subset #1, #2 and #3, as noted above, other embodiments can evaluate all subsets, at least when processing time is not a controlling factor. In this regard, figures-of-merit $\epsilon_1$ through $\epsilon_{10}$, for all ten subsets are shown in TABLE 2 below.

TABLE 2

| Subset # (k) | $\epsilon_k$ |
|---|---|
| 1 | 0.248 |
| 2 | 0.315 |
| 3 | 0.320 |
| 4 | 0.220 |
| 5 | 0.240 |
| 6 | 0.312 |
| 7 | 0.195 |
| 8 | 0.221 |
| 9 | 0.312 |
| 10 | 0.224 |

In this example, subset #7 has the smallest figure-of-merit, and thus is indicative of the desired utility of the subsets (i.e., most closely corresponds to the target voltage). In an exemplary embodiment, the result of step 460 would be to select subset #7 as the subset for this channel. That is, it would be selected as the three-electrode contact channel as having the desired utility (to most closely achieve the target output $V_t$). In embodiments using a different figure-of-merit, the subset having the desired utility can be a subset that has other than the smallest figure-of-merit. For example, it can be the largest, closest to a predetermined value, closest to a predetermined value without going over, closest to a predetermined value without going under, etc. In general, while for this case, the subset identified has having the desired utility is composed of the three closest electrode contacts to the target site of stimulation, this is not always the case, at least when N>M>3 and the given subsets often contain non-contiguous sets of electrode contacts.

Having determined the subset of a given number of electrode contacts having the desired utility for the given channel, method 700 moves from step 760 to 770, which entails repeating steps 730, 740, 750 and 760 for other values of M that are to be tested, if any. That is, if the number of electrode contacts to be used for a given channel is not fixed, the entire process can be repeated for various values of M subject to possible constraints, such as limiting M to be less than some upper limit. The subset can be chosen for the channel by selecting the subset having the lowest figure-of-merit (step 780). This chosen subset is the subset to be utilized when implementing a given channel of the cochlear implant. The subset is implemented by energizing the electrode contacts of that subset at currents that are weighted according to values of transimpedance-based data associated with those electrode contacts. More particularly, default weights for the selected channel i are derived from the $i^{th}$ column of matrix $Y_k$ where k is the selected subset of electrode contacts. The weights for the channel can be normalized by dividing each value in the column by the largest of their absolute values. Alternatively, or in addition to this, the default weights and corresponding reduced matrix $Z_k$ can serve as a starting point for further optimization. Those weights can be varied to achieve weights having a desired utility. Such variation can be achieved by, for example, the methods such as those described in U.S. Pat. App. Pub. No. US 2010/0198301 and U.S. Pat. App. Pub. No. US 2001/0288613.

In view of the above, an exemplary method includes determining respective estimated stimulation profiles $V_{elk}$ for the plurality of L stimulation sites corresponding to stimulation by respective subsets $e_k$ of electrode contacts and comparing the determined estimated stimulation profiles $V_{elk}$ to the target stimulation profile $V_{tl}$. It is noted that such determinations and comparisons can be executed without actually establishing formal vectors. In this regard, it is noted that the variables $V_{elk}$ and $V_{tl}$ as used herein, as well with other vector notations detailed herein, represent both vectors and data that can be placed into the form of a vector, and recitation of such variables does not require that the data be placed in and/or result in vectors. That is, unless otherwise noted, the variables used herein represent data in any format that can be used to implement the teachings herein and/or variations thereof.

Figure 7:
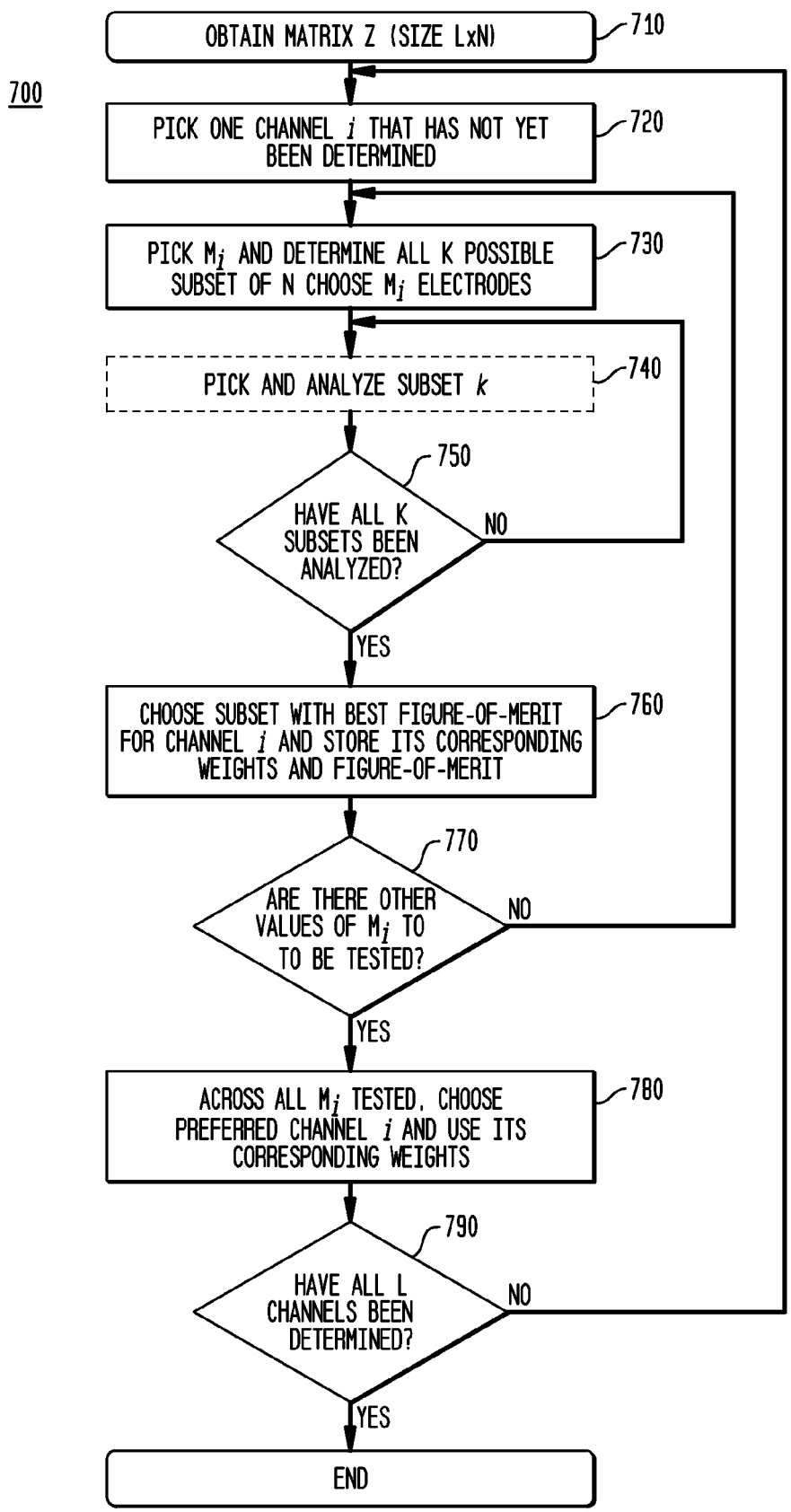
FIG. 7 is a flowchart illustrating a method for configuring a stimulating prosthesis.

It is noted that while the method of FIG. 7 details choosing a subset with a figure-of-merit having the desired utility in step 760 for each value of M, other embodiments can determine a figure-of merit for each subset for each value of M, and then choose the subset with the figure-of-merit having the desired utility after step 770. Any device, system and/or method to determine which subset to use for a given channel can be used in at least some embodiments providing that the teachings detailed herein and/or variations thereof can be practiced.

Alternatively or in addition to this, a rule can be defined to trade off the increased cost/complexity of a higher M against the corresponding improvement in figure-of-merit. For example, the RMS error might drop discontinuously when M is raised above a threshold value. In that case, the subset with the smallest M above such a threshold can be selected to define the channel.

In an exemplary embodiment, a tradeoff can be made between power consumption resulting from energizing electrode contacts and the resulting voltage profile. In an exemplary scenario, if the subset of electrode contacts having the closest estimated voltage profile to the target profile includes seven electrode contacts, but a three electrode contact subset has an estimated voltage profile that is sufficiently close to the target voltage profile, that three electrode contact subset can be selected for a given channel. Such can be the case because such can result in less power consumption because four less electrode contacts need be energized. Accordingly, the utilitarian value of the three electrode contact subset can be more desirable than that of the seven electrode contact subset even though the seven electrode contact subset has an estimated voltage profile that is closer to the target than the three electrode contact subset. In this regard, there is a method that includes selecting a subset based on factors relating to power consumption associated with energizing electrode contacts.

Accordingly, in an exemplary embodiment, there is a method that includes obtaining data that is based on one or more factors relating to prosthesis internal performance when energizing the first subset of electrodes to apply estimated voltages to various respective sites, and generating configuration data for the prosthesis based on this data. By "factors relating to prosthesis internal performance," it is meant performance characteristics associated with the inner workings of the prosthesis. This as compared to the external performance of the prosthesis, such as the performance characteristics with evoking the hearing percept (e.g., how close the estimated voltage profile corresponds to the target profile), additional details of which are discussed below. Exemplary prosthesis internal performance factors include, by way of example and not by way of limitation, the power consumption data for given subsets of electrode contacts, as detailed above, time required to provide the simulation from the contacts (where some subsets may permit a stimulation to be executed faster than other subsets), thermal energy generated by the prosthesis (e.g., by the battery), which may include an rate of thermal energy generation and/or a quantity of thermal energy generation over one or more given temporal periods), likelihood of failure (e.g., due to the number of times certain transistors of the prosthesis are activated, etc. Any one or more prosthesis internal performance factors may be taken into account when generating the configuration data.

In a similar vein, at least some of the features detailed above pertaining to the performance of the prosthesis vis-à-vis the estimated voltages applied to the stimulation sites may be characterized as factors relating to prosthesis external performance. By "factors relating to prosthesis external performance," it is meant performance characteristics associated with the external workings of the prosthesis. Exemplary prosthesis external performance factors include, by way of example, the respective estimated (target) voltages for the stimulation sites be applied by a subset of electrode contacts. Such exemplary prosthesis external performance factors may comprise data indicative of a comparison between the respective estimated (target) voltages for the stimulation sites be applied by a subset of electrode contacts and data based on respective target voltages for the respective sites. Referring back to the example above, it can be seen that the three-electrode contact channel (subset of three electrode contacts) having the desired utility is centered about electrode contact 3 (subset #7), which corresponds to the electrode contact most proximate site 5. In an exemplary embodiment, the subset having the desired utility can not necessarily be so centered, such as can be the case with respect to the scenario where it is desired to reduce power consumption as a tradeoff against closeness of the estimated voltages to the target voltages.

A stimulating device can be configured to use any subset of electrode contacts having utility in some embodiments, where the utility can or can not directly correspond to closeness of the estimated voltage profile to the target voltage profile.

In addition to the procedure described to determine the electrode contact subset having the desired utility across all possible subsets of size M, other approaches can be implemented based on any of a number of well known optimization algorithms (e.g., genetic algorithms, linear programming) without deviating from the principles of the technology disclosed herein.

Having determined the subset of electrode contacts for the given channel and the associated weights for that subset, method 700 proceeds to step 790, where a determination is made as to whether a subset and weights thereof for each channel has been selected. If there are additional channels for which a determination has not yet been made, the method proceeds from step 790 to step 720, and steps 720, 730, 740, 750, 760, 770, 780 and 790 are repeated until a determination has been made for all L channels.

Figure 9:
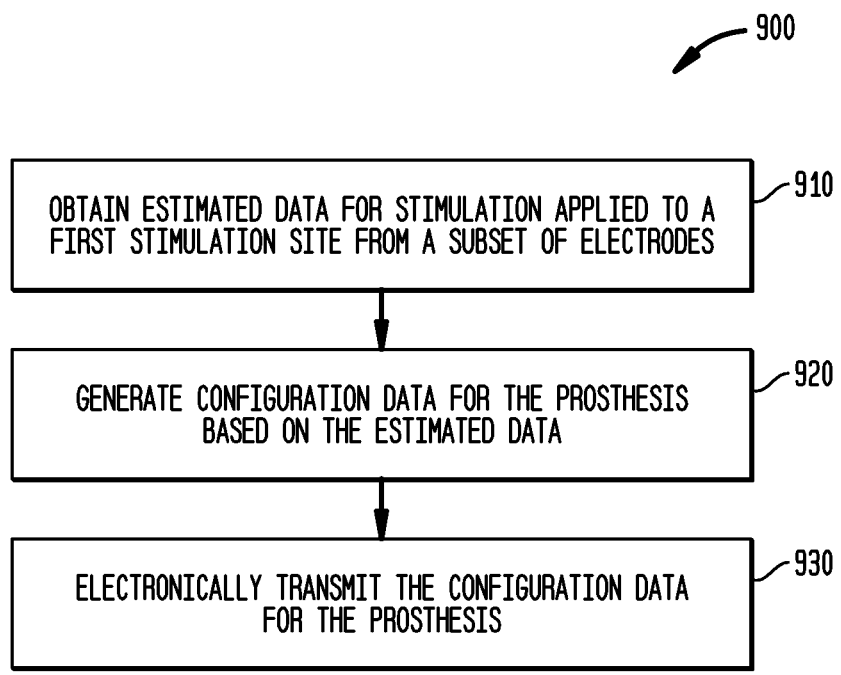
FIG. 9 is a flowchart illustrating an exemplary method for providing configuration data for a prosthesis having a plurality of electrode contacts.

FIG. 9 depicts an exemplary flowchart representing a method 900 of providing configuration data for a prosthesis having a plurality of electrode contacts. Step 910 of method 900 entails obtaining estimated data (e.g., the actual voltage data detailed above) for stimulation applied to a first stimulation site from a subset of electrode contacts of the plurality of electrode contacts numbering less than the total number of electrode contacts of the prosthesis. In this exemplary embodiment, the estimated data is based on respective transimpedance-based data for the first stimulation site and at least one additional site and one or more respective target voltages for the first and additional sites. Step 920 entails generating configuration data for the prosthesis based on the estimated data. Steps 910 and 920 can be performed according to method 700 as detailed above, and/or variations thereof. Step 930 entails electronically transmitting configuration data for the prosthesis, whereby the configuration data configures the prosthesis to stimulate the first stimulation site via the subset of electrode contacts. In an exemplary embodiment, step 930 can be executed by transmitting the data to a memory (volatile and/or nonvolatile) or memory device that is connected, either permanently or removably, to the device used to generate the configuration data. By way of example, transmission can be from a personal computer on which programming resides to execute one or more of the method steps detailed herein and/or variations thereof, to a flash drive or the like connected to that personal computer via a USB port. In an exemplary embodiment, step 930 can be executed by transmitting the data via a wired or wireless connection to a remote device (e.g., remote computer or cochlear implant connected to a device that permits reception of the transmitted data) or a remote center (e.g., medical center), etc. It is further noted that in an exemplary embodiment, one or more or all of the method steps detailed herein and/or variations thereof may be executed by an implant, such as, for example, the cochlear implant 100 detailed above with respect to FIG. 1. In an exemplary embodiment, one or more or all of the method steps herein and/or variations thereof may be executed by the external component 142 (e.g., the BTE device 126 or a button sound processor or the like) and/or the internal component 144, or another component. Accordingly, some embodiments include an external component (e.g., the BTE device 126 or a button sound processor or the like) and/or an internal component configured execute one or more or all of the method steps herein and/or variations thereof. In some embodiments, one or more or all of the method steps herein and/or variations thereof may be executed without direct intervention and/or without intervention at all and/or without the assistance of an audiologist or the like. That is, some embodiments are such that a recipient initiates one or more or all of the method steps herein and/or variations thereof utilizing an implant configured to automatically execute one or more or all of the method steps herein and/or variations.

Embodiments of the teachings detailed herein and/or variations thereof can take the form of hardware, firmware and/or software. In some embodiments, the technology is implemented in firmware, resident software, microcode, a Field Programmable Gate Array (FPGA), graphics processing unit (GPU), or Application-Specific Integrated Circuit (ASIC), etc. In some embodiments, at least for, for real-time or near real-time use, FPGA or GPU implementation can be utilized.

In the same vein, some embodiments of the teachings detailed herein and/or variations thereof can take the form of a computer program product comprising program modules accessible from computer-usable or computer-readable medium storing program code for use by or in connection with one or more computers, processors, or instruction execution system. For the purposes of this description, a computer-usable or computer readable medium can be any apparatus that can contain, store, communicate, propagate, or transport the program for use by or in connection with the instruction execution system, apparatus, or device. The medium can be non-transitory (e.g., an electronic, magnetic, optical, electromagnetic, infrared, or semiconductor system (or apparatus or device)) or transitory (e.g., a propagation medium). Examples of a non-transitory computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. Both processors and program code for implementing each as aspect of the technology can be centralized or distributed (or a combination thereof) as known to those skilled in the art.

Figure 10:
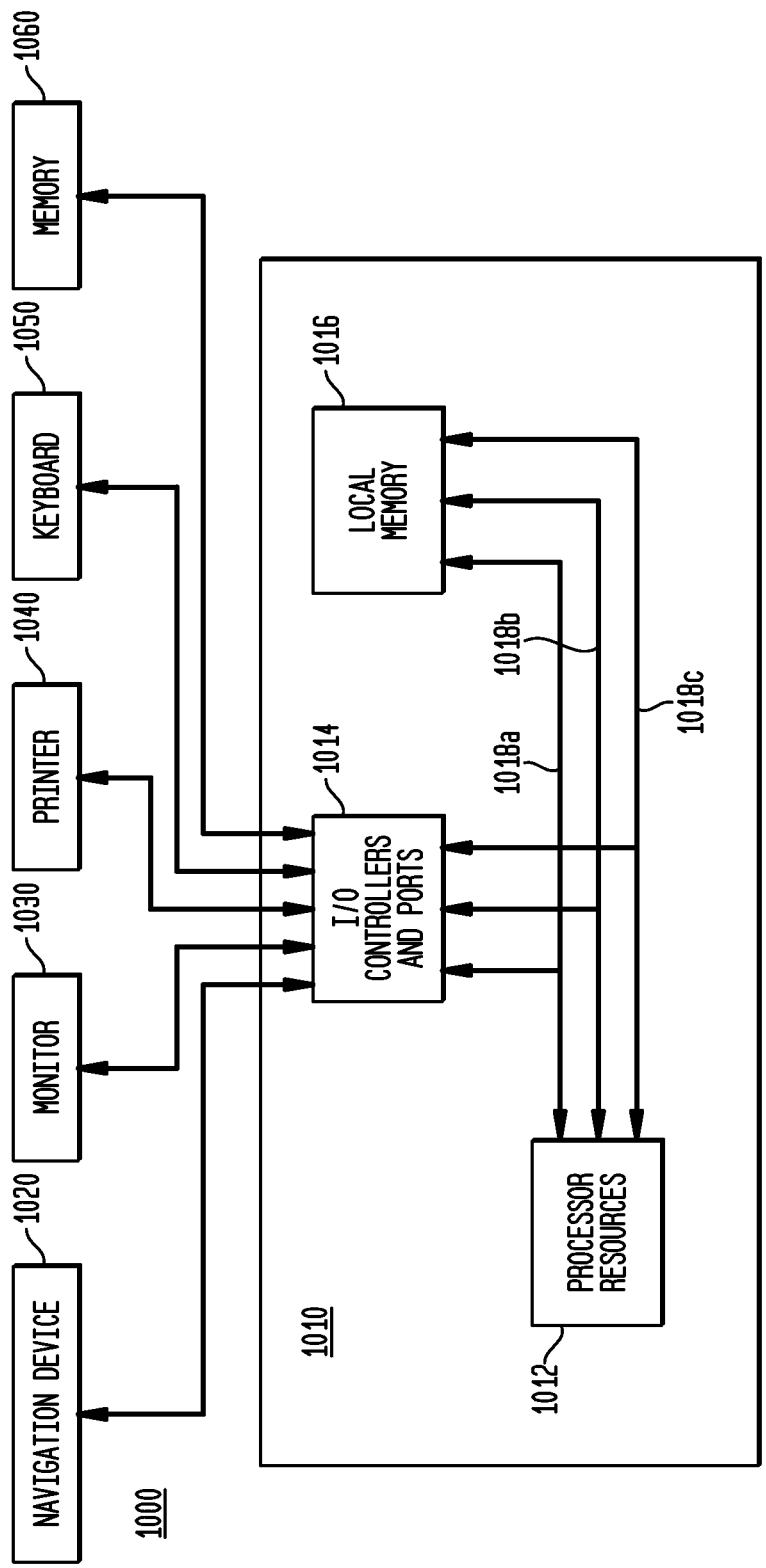
FIG. 10 is a data processing system suitable for storing a computer program product according to an exemplary embodiment and for executing the program code of the computer program product.

FIG. 10 depicts a functional diagram of a data processing system 1000 configured for storing a computer program product of the present technology and for executing the program code of the computer program product. In this exemplary embodiment, system 1000 includes least one processor (e.g., processor resources 1012) coupled directly and/or indirectly to memory elements through a system bus (e.g., 1018 comprising data bus 1018a, address bus 1018b, and control bus 1018c). The memory elements can include local memory (e.g., 1016) employed during actual execution of the program code, bulk storage (e.g., 1060), and cache memories (e.g., including cache memory as part of local memory or integrated into processor resources) that provide temporary storage of at least some program code in order to reduce the number of times code must be retrieved from bulk storage during execution. Input/output or I/O devices (including but not limited to keyboards 1050, displays 1030, pointing devices 1020, etc.) can be coupled to the system either directly or through intervening I/O controllers (e.g., 1014). Network adapters can also be coupled to the system to enable the data processing system to become coupled to other data processing systems or re-mote printers or storage devices through intervening private or public networks. Modems, cable modem and Ethernet cards are just a few of the currently available types of network adapters. Such systems can be centralized or distributed, e.g., in peer-to-peer and client/server configurations. In some implementations, the data processing system is implemented using one or both of FPGAs and ASICs.

In an exemplary embodiment, system 1000 includes a memory (such as, for example, local memory 1016) that corresponds to a non-transitory computer readable medium having recorded thereon, a computer program for generating configuration data for a prosthesis configured to stimulate a first stimulation site l of a plurality of L stimulation sites, the prosthesis comprising a plurality N of stimulation electrode contacts. The computer program is configured to receive input such as target stimulation profile data representative of $V_{tl}=[v_{t1} \ldots v_{tL}]$ for the plurality of L stimulation sites. This input can be in the form of a vector or any other input that will permit the program to utilize the input to execute the methods detailed herein and/or variations thereof. By way of example, target stimulation profile data representative of $V_{tl}$ can be simply input indicating that the target voltage should be a given number for a given location without input for the remaining locations, and the computer can utilize default values (e.g., zero) for the remaining locations and/or can query whether there are any other non-zero values at other locations.

The computer program can be configured to further receive input corresponding to:

(i) data representative of respective L×N or L×M transimpedance matricies $Z_k$ for respective subsets of electrode contacts $e_k$ corresponding to a subset of electrode contacts including a quantity of electrode contacts numbering less than N, the matricies having columns corresponding to each of the N electrode contacts or M electrode contacts, respectively, where M corresponds to a quantity of electrode contacts numbering less than N, and rows corresponding to each of the sites L;

(ii) data representative of respective N×L or M×L transadmittance matricies $Y_k$ for the respective subsets of electrode contacts that are inverses or pseudo-inverses of the respective transimpedance matrix $Z_k$; and/or (iii) data representative of respective L×L matricies $Z_k Y_k$ corresponding to $Z_k$ multiplied by $Y_k$.

In an exemplary embodiment, this data can be in the form of an array or the like, or can be in the form of a vector or the like, or in the form of a matrix or the like. Any device, system and/or method of providing the input can be used to practice some embodiments detailed herein and/or variations thereof.

It is noted that in some embodiments, the computer program is configured to/includes code to manipulate the input into a format conducive to the matrix manipulations detailed herein and/or variations thereof.

The computer program further includes code for determining respective estimated stimulation profiles for the plurality of L stimulation sites corresponding to stimulation by the respective subset of electrode contacts, and code for comparing the determined estimated stimulation profiles to the target stimulation profile data. The computer program further includes code for generating the configuration data for the prosthesis based on the comparison.

While various embodiments have been described above, it should be understood that they have been presented by way of example only, and not limitation. It will be apparent to persons skilled in the relevant art that various changes in form and detail can be made therein without departing from the scope of the teachings. Thus, the breadth and scope of the teachings herein should not be limited by any of the above-described exemplary embodiments, but should be defined only in accordance with the following claims and their equivalents.

What is claimed is:

1. A method of configuring a prosthesis having two or more electrode contacts, comprising:
   configuring the prosthesis to provide stimulation to a first tissue site from a subset of electrode contacts based on data based on a comparison of first data to second data, wherein
   the first data is based on respective estimated voltages for the first site and one or more of additional respective sites to be applied by the subset of electrode contacts, the respective estimated voltages being based on empirical stimulation data for the first and additional sites, and
   the second data is based on respective target voltages for the first and additional sites, respectively.

2. The method of claim 1, wherein the empirical data is transimpedance-based data for the first and additional sites.

3. The method of claim 2, wherein the transimpedance-based data is based on an inverse or a pseudo-inverse of transimpedance data for the first and additional sites.

4. The method of claim 3, wherein the transimpedance-based data is based on an inverse or a pseudo-inverse of a transimpedance matrix for the first and additional sites.

5. The method of claim 1, wherein the first data and the second data are data vectors constructed of respective data for the first and additional sites.

6. The method of claim 2, wherein the respective estimated voltages are further based on the respective target voltages for the first and additional sites.

7. The method of claim 1, wherein the respective estimated voltages are based on respective electrode contact currents to be applied by the electrode contacts of the subset of electrode contacts to achieve, based on the empirical data, the target voltages for the first and additional sites based on the empirical data.

8. The method of claim 1, wherein the action of configuring the prosthesis to provide stimulation to a first site is further based on a comparison of power consumption data for the subset of electrode contacts.

9. The method of claim 1, wherein the respective estimated voltages are based on data based on the multiplication of transimpedance data and transadmittance data.

10. The method of claim 9, wherein the data on which the respective estimated voltages is based is further based on the multiplication of the multiplied transimpedance data and transadmittance data by the respective target voltages for the first and additional respective sites.

11. The method of claim 1, wherein the estimated voltages are first estimated voltages, wherein the subset of electrode contacts is a first subset of electrode contacts, and wherein the action of configuring the prosthesis to provide stimulation to a first site is further based on a comparison of third data to the second data, wherein
   the third data is based on respective second estimated voltages for the first and additional respective sites to be applied by a second subset of electrode contacts different from the first subset of electrode contacts, the respective second estimated voltages being based on the empirical stimulation data for the first and additional respective sites.

12. The method of claim 11, wherein the action of configuring the prosthesis to provide stimulation to a first site is further based on a comparison of (i) data based on the comparison of the first data to the second data and (ii) data based on the comparison of the third data to the second data.

13. The method of claim 12, wherein the action of configuring the prosthesis to provide stimulation to a first site is further based on data based on (i) a comparison of fourth data based on the comparison of the first data to the second data and (ii) fifth data based on the comparison of the third data to the second data.

14. The method of claim 13, wherein the action of configuring the prosthesis to provide stimulation to a first site is further based on data based on a determination that the fourth data represents data indicative of the first data being more similar in comparison to the second data relative to that of the third data in comparison to the second data.

15. The method of claim 13, wherein:
the action of configuring the prosthesis to provide stimulation to a first site is further based on data based on a determination that the fourth data represents data indicative of the first data being more different in comparison to the second data relative to that of the third data in comparison to the second data; and
the action of configuring the prosthesis to provide stimulation to the first site is further based on a determination that power consumption by the first subset of electrode contacts is less than the power consumption of the second subset of electrode contacts.

16. A method of providing configuration data for a prosthesis having a plurality of electrode contacts, comprising:
applying stimulation to a first stimulation site from a subset of electrode contacts of the plurality of electrode contacts;
obtaining first estimated data for the stimulation applied to the first stimulation site from the subset of electrode contacts, the first estimated data based on:
respective transimpedance-based data for the first stimulation site and at least one additional stimulation site based on empirical results of the applied stimulation to the first stimulation site; and
one or more respective target voltages for the first and additional sites; and
generating configuration data for the prosthesis based on the first estimated data, wherein the prosthesis is operable to be configured by the configuration data to stimulate the first stimulation site via the subset of electrode contacts.

17. The method of claim 16, wherein:
the configuration data configures the prosthesis to stimulate the first stimulation site via the subset of electrode contacts for the respective target voltages for the first and additional sites.

18. The method of claim 16, wherein obtaining the first estimated data comprises:
obtaining one or more respective current values to be applied by the respective electrode contacts of the subset of electrode contacts to achieve the target voltages for the first and additional sites based on the transimpedance-based data and the one or more respective target voltages.

19. The method of claim 18, wherein the transimpedance-based data is transadmittance data, and wherein obtaining one or more respective current values comprises:

multiplying the transadmittance data by the one or more respective target voltages.

20. The method of claim 19, wherein the transadmittance data is an inverse or a pseudo-inverse of a transimpedance matrix, and wherein the one or more respective target voltages are a vector made up of the one or more respective target voltages.

21. The method of claim 19, wherein the action of generating configuration data for the prosthesis based on the first estimated data includes:
multiplying (i) the transimpedance data by (ii) the transadmittance data multiplied by the one or more respective target voltages.

22. The method of claim 20, wherein the transimpedance data is a transimpedance matrix, and wherein the one or more respective target voltages are a vector made up of the one or more respective target voltages.

23. The method of claim 22, wherein:
the subset of electrode contacts is a first subset of electrode contacts; and
the method further comprises:
obtaining second estimated data for stimulation applied to the first stimulation site from a second subset of electrode contacts of the plurality of electrode contacts numbering less than the total number of electrode contacts and different from that of the first subset, the second estimated data being based on:
the respective transimpedance-based data for the first and additional sites; and
the one or more respective target voltages for the first and additional sites;
comparing the first estimated data to the second estimated data.

24. The method of claim 23, wherein the action of generating configuration data for the prosthesis further comprises selecting the first subset based on the comparison of the first estimated data to the second estimated data.

25. The method of claim 24, wherein selecting the first subset based on the comparison of the first estimated data to the second estimated data includes determining that the first estimated data
represents data indicative of the first subset providing stimulation to the first and additional sites that is closer to the target voltage for the first and additional sites than the stimulation provided by the second subset to the first and additional sites.

26. A non-transitory computer readable medium having recorded thereon a computer program for generating configuration data for a prosthesis configured to stimulate a first stimulation site l of a plurality of L stimulation sites, the prosthesis comprising a plurality N of stimulation electrode contacts, when provided with:
target stimulation profile data representative of $V_{tl}=[v_{t1} \ldots v_{tL}]$ for the plurality of L stimulation sites;
at least one of:
respective data representative of L×N or L×M transimpedance matricies $Z_k$ for respective subsets of electrode contacts $e_k$ including a quantity of electrode contacts numbering less than N, the matricies having columns corresponding to each of the N electrode contacts or M electrode contacts, respectively, where M corresponds to a quantity of electrode contacts numbering less than N, and rows corresponding to each of the sites L,
respective data representative of N×L or M×L transadmittance matricies $Y_k$ for the respective subsets of electrode contacts that are inverses or pseudo-inverses of the respective transimpedance matrix $Z_k$, or respective data representative of L×L matricies $Z_k Y_k$ corresponding to $Z_k$ multiplied by $Y_k$;

the computer program comprising:

code for determining respective estimated stimulation profiles $V_{elk}$ for the plurality of L stimulation sites corresponding to stimulation by the respective subset of electrode contacts;

code for comparing the determined estimated stimulation profiles $V_{elk}$ to the target stimulation profile $V_{ti}$; and code for generating the configuration data for the prosthesis based on the comparison.

27. The non-transitory computer readable medium of claim 26, wherein the code for determining respective estimated stimulation profiles $V_{elk}$ for the plurality of L stimulation sites corresponding to stimulation by the respective subset of electrode contacts further includes at least one of:

code for obtaining respective current profiles $I_{tk}$ for the subsets of electrode contacts by multiplying the respective transadmittance matricies $Y_k$ by the target stimulation profile $V_{tl}$ and multiplying the respective transimpedance matrix $Z_k$ by the respective current profile; or code for multiplying the result of the multiplication of matricies $Z_k Y_k$ by the target stimulation profile $V_{tl}$.

28. The non-transitory computer readable medium of claim 26, wherein the code for comparing the determined estimated stimulation profiles $V_{elk}$ to the target stimulation profile $V_{tl}$ includes code for identifying one of the estimated stimulation profiles $V_{elk}$ that meritoriously replicates a target stimulation profile $V_{tl}$, and wherein the code for generating the configuration data includes code for selecting the subset of the subset of electrode contacts $e_k$ corresponding to the identified one of the estimated stimulation profiles $V_{elk}$.

29. The non-transitory computer readable medium of claim 26, wherein the code for comparing the determined estimated stimulation profiles $V_{elk}$ to the target stimulation profile $V_{tl}$ includes code for determining a figure-of-merit for the respective estimated stimulation profiles based on the target stimulation profile, and wherein the code for generating configuration data includes code for selecting the subset of the subset of electrode contacts $e_k$ corresponding to the estimated stimulation profile having a figure-of-merit that most closely corresponds to a desired figure-of-merit.

30. The non-transitory computer readable medium of claim 26, wherein the computer program further comprises:

code for comparing the determined estimated stimulation profiles $V_{elk}$ to the target stimulation profile $V_{tl}$ by identifying one of the estimated stimulation profiles $V_{elk}$ that most closely corresponds to the target stimulation profile $V_{tl}$; and code for generating configuration data by selecting the subset of the subset of electrode contacts $e_k$ corresponding to the identified one of the estimated stimulation profiles $V_{elk}$.

31. A non-transitory computer readable medium having recorded thereon a computer program for generating configuration data for configuring a prosthesis having two or more electrode contacts to provide stimulation to a first tissue site from a subset of the electrode contacts, when provided with:

first data that is based on one or more factors relating to prosthesis external performance related to energizing the first subset of electrodes to apply respective first estimated voltages to the first site and one or more additional respective sites; and second data that is based on one or more factors relating to prosthesis internal performance when energizing the first subset of electrodes to apply the first estimated voltages to the first and additional respective sites;

the computer program comprising:

code for generating configuration data for the prosthesis based on the first data and the second data, wherein the prosthesis is operable to be configured by the configuration data to stimulate the first stimulation site via a second subset of electrode contacts different from the first subset of electrode contacts.

32. The non-transitory computer readable medium of claim 31, wherein:

the one or more factors relating to prosthesis internal performance include power consumption data for the first subset of electrode contacts.

33. The non-transitory computer readable medium of claim 32, wherein:

the code for generating configuration data for the prosthesis further includes code for generating configuration data based on data based on a determination that power consumption by the first subset of electrode contacts is greater than the power consumption of the second subset of electrode contacts.

34. The non-transitory computer readable medium of claim 31, wherein:

the first data is based on a comparison of third data to fourth data, wherein the third data is based on the respective first estimated voltages for the first site and one or more of additional respective sites to be applied by the first subset of electrode contacts, the respective first estimated voltages being based on empirical stimulation data for the first and additional sites, and wherein the fourth data is based on respective target voltages for the first and additional sites, respectively;

data provided to the computer program further includes:

fifth data that is based on respective second estimated voltages for the first and additional respective sites to be applied by the second subset of electrode contacts, the respective second estimated voltages being based on the empirical stimulation data for the first and additional respective sites; and sixth data that is based on one or more factors relating to prosthesis internal performance when energizing the second subset of electrodes to apply the second estimated voltages to the first and additional respective sites, wherein the code for generating configuration data for the prosthesis further includes code for generating configuration data based on:

data based on a comparison of (i) the first data to (ii) data based on a comparison of the fifth data to the fourth data; and data based on a comparison of the second data to the sixth data.

35. The non-transitory computer readable medium of claim 34, wherein:

the code for generating configuration data for the prosthesis further includes code for generating configuration data based on data based on a determination that the third data is more similar in comparison to the fourth data relative to that of the fifth data in comparison to the fourth data.

36. The non-transitory computer readable medium of claim 34, wherein:
    the code for generating configuration data for the prosthesis further includes code for generating configuration data based on data based on a determination that the third data is more different in comparison to the fourth data relative to that of the fifth data in comparison to the fourth data.

37. The non-transitory computer readable medium of claim 31, wherein:
    the computer program includes code for obtaining the first and second data.

* * * * *